United States Patent
Milman et al.

[11] Patent Number: 6,075,599
[45] Date of Patent: *Jun. 13, 2000

[54] OPTICAL DEVICE WITH ENTRANCE AND EXIT PATHS THAT ARE STATIONARY UNDER DEVICE ROTATION

[75] Inventors: Uri Milman, Migdal Haemek; Dario Cabib, Timrat, both of Israel

[73] Assignee: Applied Spectral Imaging Ltd., Migdal Haemek, Israel

[*] Notice: This patent is subject to a terminal disclaimer.

[21] Appl. No.: 09/012,412

[22] Filed: Jan. 23, 1998

Related U.S. Application Data

[63] Continuation-in-part of application No. 08/942,122, Oct. 1, 1997, which is a continuation-in-part of application No. 08/571,047, Dec. 12, 1995, Pat. No. 5,784,162, which is a continuation-in-part of application No. 08/329,019, Feb. 21, 1995, Pat. No. 5,539,517, which is a continuation-in-part of application No. 08/107,673, Aug. 18, 1993, abandoned.

[51] Int. Cl.[7] .................................................... G01B 9/02
[52] U.S. Cl. ............................................................ 356/346
[58] Field of Search .................................... 356/345, 346

[56] References Cited

U.S. PATENT DOCUMENTS

| 3,814,935 | 6/1974 | Kissel | 250/231.14 |
| 3,861,788 | 1/1975 | Webster | 356/418 |
| 5,539,517 | 7/1996 | Cabib et al. | 356/345 |

*Primary Examiner*—Samuel A. Turner
*Attorney, Agent, or Firm*—Mark M. Friedman

[57] ABSTRACT

An rotating optical device in which the angular relationship of the exit beam to the incident beam is independent of the degree of rotation of the device. Two optical elements are defined by planes that intersect at a 45° angle. A third optical element is defined by a plane that bisects the 45° angle. The device is rotated about the line included by all three planes. In an embodiment of the device configured as a Sagnac interferometer, the first two optical elements are reflectors and the third element is a beamsplitter. Preferably, up to eight such interferometers are mounted on the same rotating platform and with the same rotational axis, for extended spectral bandwidth. The scope of the invention also includes spectral imaging devices based on such interferometers.

17 Claims, 8 Drawing Sheets

OPTICAL DEVICE WITH ENTRANCE AND EXIT PATHS THAT ARE STATIONARY UNDER DEVICE ROTATION

This is a continuation in part of U.S. patent application Ser. No. 08/942,122. filed Oct. 1, 1997, which is a continuation in part of U.S. patent application Ser. No. 08/571,047, filed Dec. 12, 1995, now U.S. Pat. No. 5,784,162 which is a continuation in part of U.S. patent application Ser. No. 08/329,019, filed Feb. 21, 1995, now U.S. Pat. No. 5,539,517, which is a continuation in part of U.S. patent application Ser. No. 08/107,673, filed Aug. 18, 1993, now abandoned.

FIELD AND BACKGROUND OF THE INVENTION

The present invention relates to optical devices and, more particularly, to an optical device that rotates with respect to an incident beam of light in such a way that the exiting beam remains substantially stationary as the device rotates.

U.S. Pat. No. 5,539,517 to Cabib et al., which is incorporated by reference for all purposes as if fully set forth herein, teaches a variety of spectral imaging devices based on interferometers. Among these interferometers is the Sagnac interferometer illustrated in FIG. 6 of that patent. As explained in the text of that patent with reference to FIGS. 7 and 8, this Sagnac interferometer can be used in two different modes. FIG. 7 illustrates a non-moving mode, in which the optical path difference within the interferometer is scanned by scanning the angle with which the incident beam enters the interferometer. FIG. 8 illustrates a moving mode, in which the optical path difference is scanned by rotating the interferometer as a whole with respect to the incident beam.

To maximize the spectral resolution of the systems of Cabib et al., it is important that the range of optical path differences scanned be as large as possible. The major limiting factor in the optical path difference range of a Sagnac interferometer is "vignetting". As the interferometer is rotated with respect to an incident beam, the exiting beam also moves. There is thus a widely recognized need for, and it would be highly advantageous to have, a Sagnac interferometer having minimal motion of the exiting beam as the interferometer is rotated with respect to the incident beam to scan optical path differences.

SUMMARY OF THE INVENTION

According to the present invention there is provided an optical device including: (a) a first optical element defining a first plane; (b) a second optical element defining a second plane and fixed rigidly with respect to the first optical element, the first and second planes intersecting, along an axis, at an angle of between about 42 degrees and about 48 degrees; (c) a third optical element defining a third plane, the optical element being fixed rigidly with respect to the first and second optical elements so that the axis is included in the third plane; and (d) a mechanism for rotating the first, second and third optical elements rigidly about the axis.

According to the present invention there is provided a method for simultaneously measuring the spectral intensity as a function of wavelength of all the pixels of a two-dimensional scene while detecting a real and stationary image of the scene, the method including the steps of: (a) collecting incident light simultaneously from all points of the two-dimensional scene using collimating optics; (b) passing the incident collimated light through an interferometer system including: (i) a first element defining a first plane, (ii) a second element defining a second plane and fixed rigidly with respect to the first element, the first and second planes intersecting, along an axis, at an angle of between about 42 degrees and about 48 degrees, and (iii) a third element defining a third plane and fixed rigidly with respect to the first and second elements so that the axis is included in the third plane, so that the light is first split into two coherent beams which travel along different optical paths inside the interferometer and then the two coherent beams recombine to interfere with each other to form an exiting light; (c) passing the exiting light through a focusing optical system which focuses the exiting light on a detector having an array of detector elements, so that at each instant each of the detector elements is the image of one and always the same pixel of the scene for the entire duration of the measurement, so that the real image of the scene is stationary on the detector array at any time during the measurement the image is still visible and recognizable, and so that each of the detector elements produces a signal which is a particular linear combination of light intensity emitted by the pixel at different wavelengths, wherein the linear combination is a function of instantaneous optical path difference; (d) rotating the elements of the interferometer system rigidly about the axis, so that the optical path difference between the two coherent beams generated by the interferometer system is scanned simultaneously for all the pixels of the scene; and (e) recording the signals of each of the detector elements as functions of time using a recording device.

According to the present invention there is provided a method for simultaneously measuring the spectral intensity as a function of wavelength of all the pixels of a two-dimensional scene located at infinity while detecting a real and stationary image of the scene, the method including the steps of: (a) collecting naturally collimated incident light simultaneously from all points of the two-dimensional scene; (b) passing the incident naturally collimated light through an interferometer system including: (i) a first element defining a first plane, (ii) a second element defining a second plane and fixed rigidly with respect to the first element, the first and second planes intersecting, along an axis, at an angle of between about 42 degrees and about 48 degrees, and (iii) a third element defining a third plane and fixed rigidly with respect to the first and second elements so that the axis is included in the third plane, so that the light is first split into two coherent beams which travel along different optical paths inside the interferometer and then the two coherent beams recombine to interfere with each other to form an exiting light; (c) passing the exiting light through a focusing optical system which focuses the exiting light on a detector having an array of detector elements, so that at each instant each of the detector elements is the image of one and always the same pixel of the scene for the entire duration of the measurement, so that the real image of the scene is stationary on the detector array at any time during the measurement the image is still visible and recognizable, and so that each of the detector elements produces a signal which is a particular linear combination of light intensity emitted by the pixel at different wavelengths, wherein the linear combination is a function of instantaneous optical path difference; (d) rotating the elements of the interferometer system rigidly about the axis, so that the optical path difference between the two coherent beams generated by the interferometer system is scanned simultaneously for all the pixels of the scene; and (e) recording the signals of each of the detector elements as functions of time using a recording device.

According to the present invention there is provided an apparatus for simultaneously measuring the spectral intensity as a function of wavelength of all the pixels of a two-dimensional scene while detecting a real and stationary image of the scene, including: (a) an interferometer system for receiving collected incident collimated light simultaneously from all points of the two-dimensional scene, the light being first split into two coherent beams which travel in different directions inside the interferometer and then the two coherent beams recombine to interfere with each other to form an exiting light, the interferometer system including: (i) a first element defining a first plane, (ii) a second element defining a second plane and fixed rigidly with respect to the first element, the first and second planes intersecting, along an axis, at an angle of between about 42 degrees and about 48 degrees, and (iii) a third element defining a third plane and fixed rigidly with respect to the first and second elements so that the axis is included in the third plane, the elements being rotatable about the axis so that an optical path difference between the two coherent beams generated by the interferometer system is scanned simultaneously for all the pixels of the scene; (b) a focusing optical system through which the exiting light is passed to form a focused light; (c) a detector having an array of detector elements on which the focused light is directed, so that at each instant each of the detector elements is the image of one and always the same pixel of the scene for the entire duration of the measurement, so that the real image of the scene is stationary on the plane of the detector array and so that each of the detector elements produces a signal which is a particular linear combination of light intensity emitted by the pixel at different wavelengths, wherein the linear combination is a function of the instantaneous optical path difference; and (d) a recording mechanism for receiving the signals of each of the detector elements as a function of time using a recording device.

It has been discovered that by orienting the mirrors of a Sagnac interferometer at 45 degrees with respect to each other, and choosing the axis of rotation of the interferometer to be the intersection line of the planes of the two mirrors, the exiting beam stays essentially stationary with respect to the incident beam as the interferometer is rotated. This can be demonstrated algebraically using geometric optics. It can be understood intuitively, however, with respect to three limiting cases illustrated in FIG. 1, wherein are drawn five radial lines PA, PB, PC, PD and PE. Angle APB is 22.5°. Angle APC is 45°. Angle APD is 67.5°. Angle APE is 90°.

Suppose, first, that the mirrors of a Sagnac interferometer are placed at BB' and at DD'. A ray 10 incident vertically via point F is reflected from point G to point I and then horizontally from point I via point F, along exit path 12. Now rotate the interferometer about point P so that the mirror formerly at BB' now is at AA' and the mirror formerly at DD' now is at CC'. If incident beam 10 were able to traverse the mirror now at CC' at point F, it would be reflected from point H back to point F and thence reflected along the same exit path 12 as before. Similarly, rotate the interferometer about point P so that the mirror formerly at BB' now is at CC' and the mirror formerly at DD' now is at EE'. Incident beam 10 is reflected from point F to point J and thence back to point F. If the reflected beam were able to traverse the mirror now at CC' at point F, it would continue along the same exit path 12 as before. More generally, exit beam 12 is fixed with respect to incident beam 10 for all rotational positions of the Sagnac interferometer about point P.

Although the optimum angle between the mirrors is 45 degrees, because at that angle exit beam 12 is exactly stationary, there is an acceptable range of angles around 45 degrees within which the range of vignetting is acceptably small. In practice, this range has been found to be from 42 degrees to 48 degrees.

Interferometers with specially selected rotation axes are known. For example, Ford, in U.S. Pat. No. 4,684,255, teaches a Michelson interferometer in which the axis of rotation is at the intersection of the plane of a beam-folding mirror and a plane of symmetry of a beamsplitter. Nevertheless, the concept of a rotating interferometer, or any similar optical device, with three elements that define planes that intersect along the axis of rotation, is not known in the prior art.

In a Sagnac interferometer of the present invention, the third optical element is a beamsplitter placed between the two mirrors. Typically, the beamsplitter is a semireflective layer sandwiched between two transparent, geometrically and optically identical parallelepipeds. The plane of the semireflective layer defines a plane of symmetry of the beamsplitter that includes the axis of rotation. In other words, the beamsplitter is disposed symmetrically with respect to the mirrors, much as is illustrated in FIGS. 6 and 12 of Cabib et al. The scope of the present invention includes optical devices in which any optical element, for example a filter, a polarizer, or a grating, is so disposed with respect to the mirrors.

It should be noted that in FIG. 12 of Cabib et al., the two mirrors form a 45° angle. Although it is implied in Cabib et al. that the optical path difference of the Sagnac interferometer of their FIG. 12 can be scanned by rigidly rotating the mirrors and the beamsplitter together, there is no indication of the optimal position of the axis of rotation, as taught herein.

The scope of the present invention also includes optical devices with multiple sets of mirrors disposed as taught herein with respect to the axis of rotation. Furthermore, the scope of the present invention includes spectral imaging devices similar to those of Cabib et al. but based on Sagnac interferometers of the present invention. Such spectral imaging devices, in addition to not suffering from the vignetting problem of the prior art devices, are more compact than similar spectral imaging devices based on, for example, the interferometer depicted in FIG. 14 of Cabib et al. Their stationary exit beams also give these spectral imaging devices better spatial resolution than the prior art devices, because the beams tend to remain centered in the focusing optics of the devices, where aberration is minimal.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a rotating optical device in which the exit beam is stationary with respect to the incident beam as the device rotates. Specifically, the present invention can be used as a Sagnac interferometer with a large optical path difference range for spectral imaging.

The principles and operation of an optical device according to the present invention may be better understood with reference to the drawings and the accompanying description.

Figure 1:
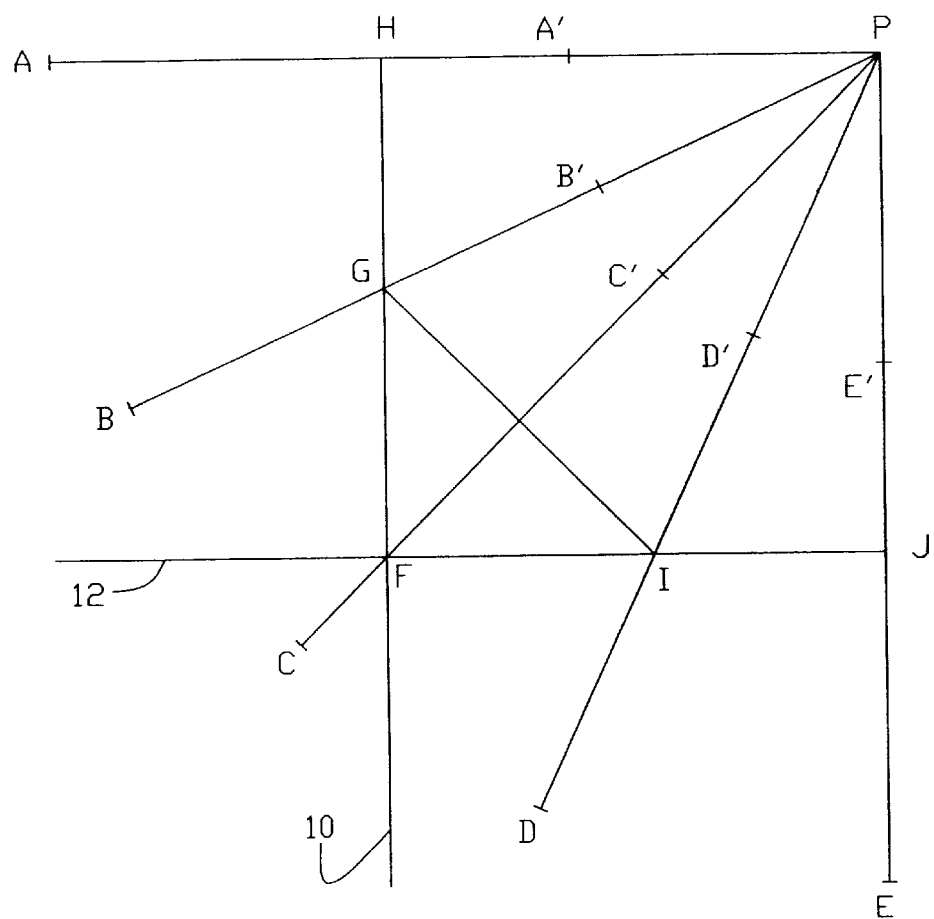
FIG. 1 illustrates the geometrical principle of the present invention.
Figure 2:
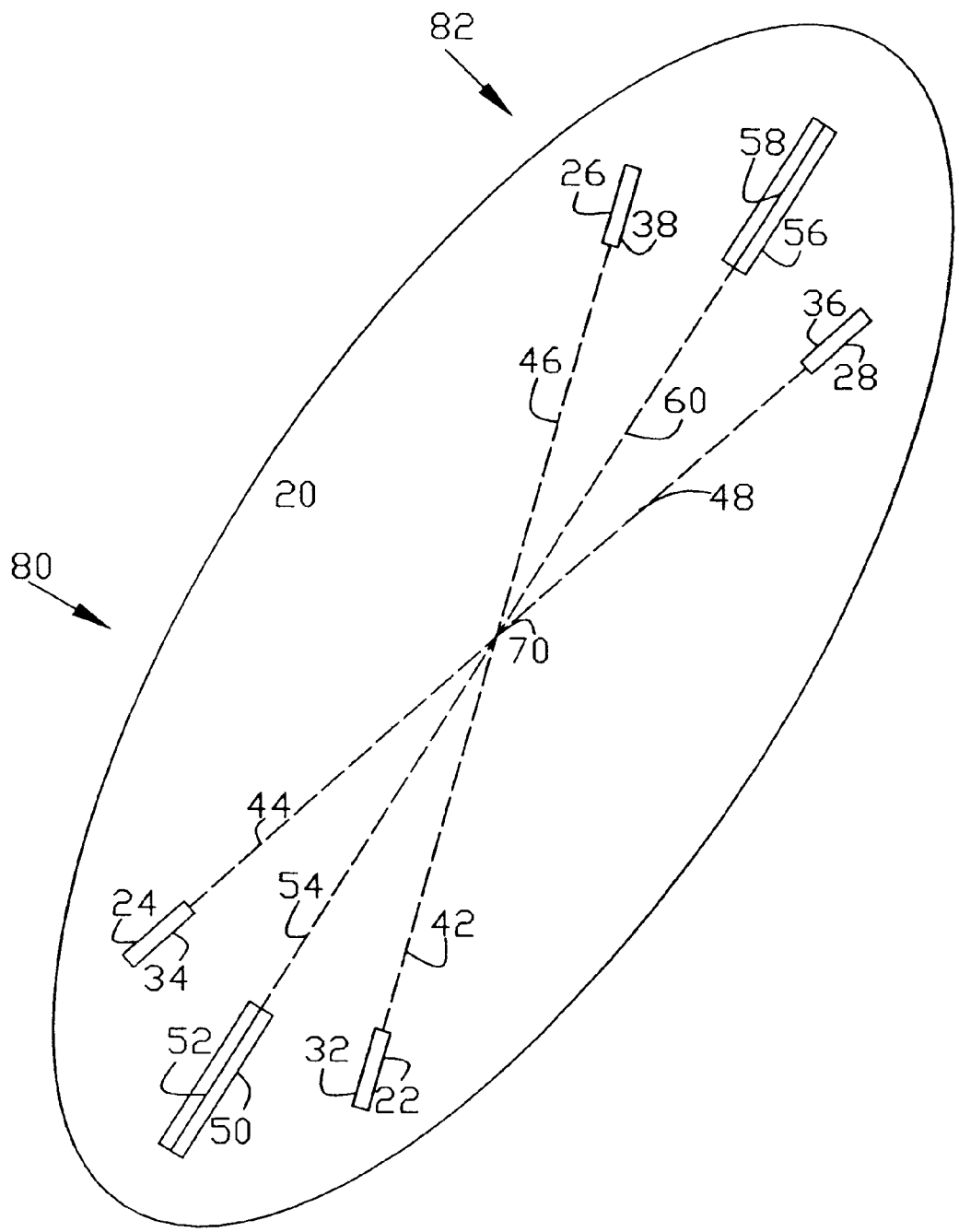
FIG. 2 is a plan view of a preferred embodiment of the present invention.
Figure 3:
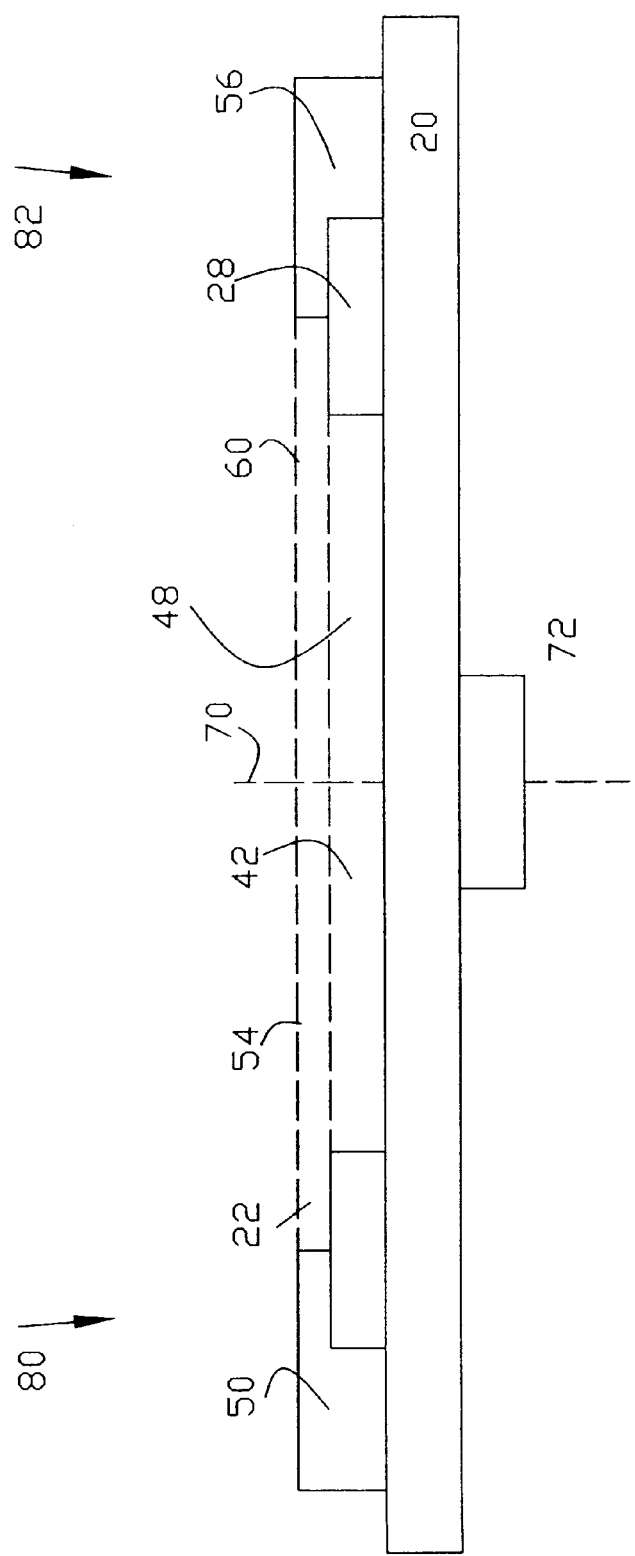
FIG. 3 is a side view of the embodiment of FIG. 2.

Referring now to the drawings, FIG. 2 is a plan view of a preferred embodiment of the present invention configured as a Sagnac interferometer, and FIG. 3 is a side view. On the flat upper surface of a platform 20 are rigidly mounted four planar mirrors 22, 24, 26 and 28, having planar reflective surfaces 32, 34, 38 and 38 respectively. Each planar surface defines a plane: surface 32 defines plane 42; surface 34 defines plane 44; surface 36 defines plane 46; and surface 38 defines plane 48. Surfaces 32, 34, 36 and 38, and corresponding planes 42, 44, 46 and 48 all are perpendicular to the upper surface of platform 20. Planes 42, 44, 46 and 48 all intersect at a common axis 70. In fact, plane 46 is an extension of plane 42 on the side of axis 70 opposite plane 42, and plane 48 is an extension of plane 44 on the side of axis 70 opposite plane 44. Planes 42 and 44 form between them a 45° angle. Similarly, planes 46 and 48 form between them a 45° angle. Also rigidly mounted on the flat upper surface of platform 20 are two beamsplitters 50 and 56. The plane of the semireflective layer 52 of beamsplitter 50 defines a plane 54. The plane of the semireflective layer 58 of beamsplitter 56 defines a plane 60. Planes 52 and 58, and associated planes 54 and 60, all are perpendicular to the upper surface of platform 20. Planes 54 and 60 intersect planes 42, 44, 46 and 48 along axis 70, so axis 70 is included in all six planes 42, 44, 46, 48, 54 and 60. Plane 54 bisects the 45° angle formed by planes 42 and 44. Plane 60 bisects the 45° angle formed by planes 46 and 48.

Below platform 20 is a stepping motor 72 that rotates platform 20 about axis 70. The various optical elements mounted on platform 20 thus constitute two rotating Sagnac interferometers. Mirrors 22 and 24 and beamsplitter 50 constitute one interferometer 80. Mirrors 26 and 28 and beamsplitter 56 constitute the other interferometer 82. To use interferometer 80, motor 70 is used to rotate platform 20 to place mirror 24 and beamsplitter 50 in the path of an incident light beam. Beamsplitter 50 splits the incident beam into two components that traverse opposite optical paths through interferometer 80. The first optical path goes from beamsplitter 50 to mirror 24, thence to mirror 22, and finally back to beamsplitter 50. The second optical path goes from beamsplitter 50 to mirror 22, thence to mirror 24, and finally back to beamsplitter 50. At beamsplitter 50, the two components are recombined to form an exit beam. The optical path difference of the two components is scanned by rotating platform 20 using motor 72. Similarly, interferometer 82 is used by rotating platform 20, using motor 70, to place mirror 28 and beamsplitter 56 in the path of the incident beam. The advantage of having two Sagnac interferometers in the same device, as illustrated, is that beamsplitters 50 and 56 can have two different optical pass bands, so that the device has a wider spectral bandwidth than either of Sagnac interferometers 80 and 82 separately. In one typical configuration, beamsplitter 50 has a passband from 450 nanometers to 750 nanometers, for imaging in the visible part of the spectrum, and beamsplitter 56 has a passband from 250 nanometers to 450 nanometers, for imaging in the near ultraviolet.

It will be appreciated that the spectral bandwidth of the present invention may be increased further by using double sided mirrors and including up to eight Sagnac interferometers on the same platform.

Figure 4:
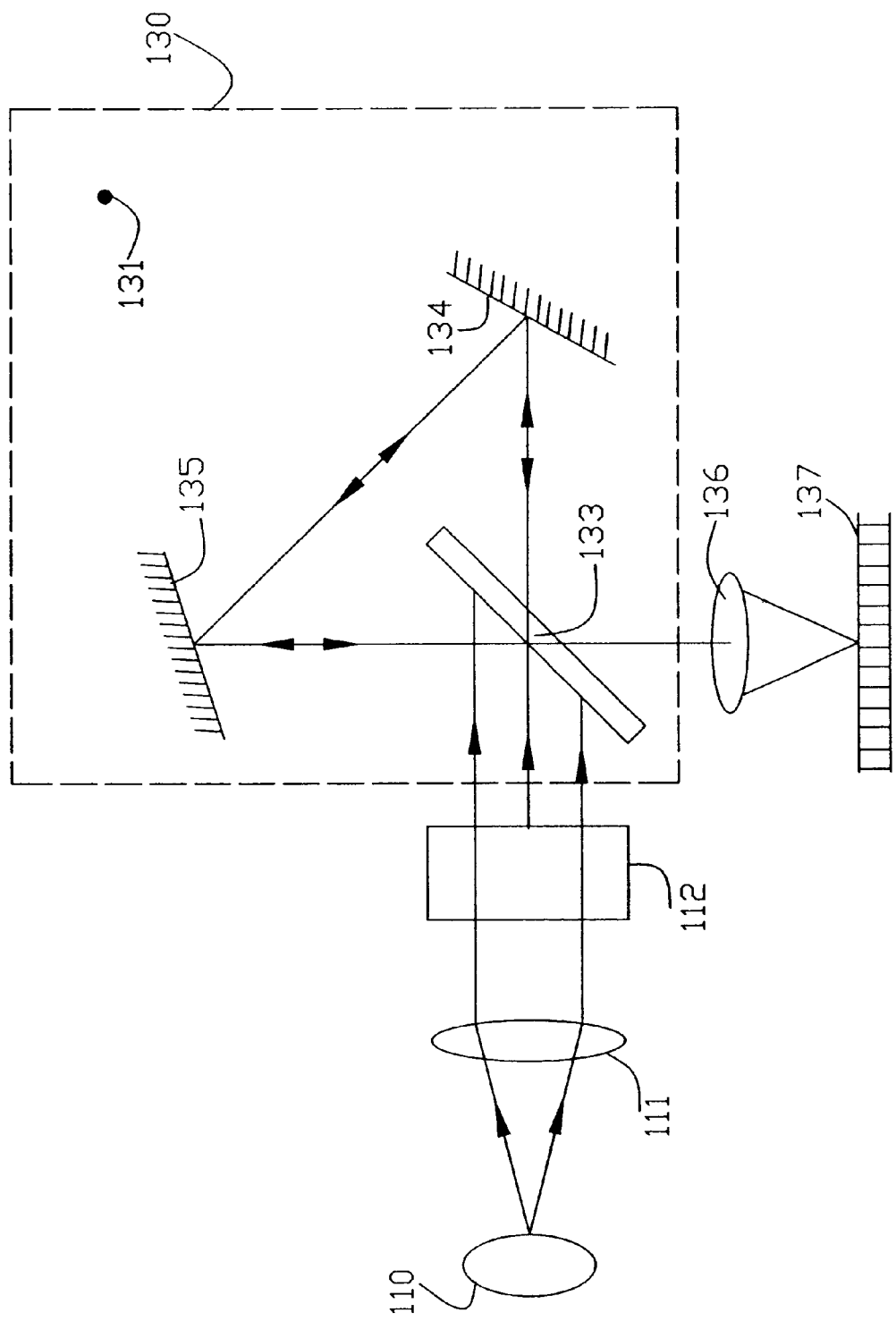
FIG. 4 is a schematic illustration of an imaging spectrometer of the present invention.

FIG. 4 is a schematic illustration of an imaging spectrometer, of the type described by Cabib et al., based on a Sagnac interferometer 130 of the present invention. The imaging spectrometer of FIG. 4 includes an optical image source 110 in which all the spectral information in all the pixels thereof, after being collimated by an optical collection system 111, is scanned by a mechanical scanner 112. Optical collection system 111 may be any suitable system for collecting and collimating light from image source 110, for example, a telescope, a microscope, a fundus camera or an endoscope. The light then enters interferometer 130, passing through a beamsplitter 133 to a first planar reflector 134, and then to a second planar reflector 135, which reflects the light back through beamsplitter 133 and then through a focusing lens 136 to a detector array 137. Interferometer 130 is rotated rigidly about an axis 131 that is perpendicular to the plane of the Figure to scan the optical path differences. This rotation of interferometer 130 changes the optical path difference through which a collimated beam from a pixel reaches a specific detector of array 137, without changing the detector on which the pixel is focused. Scanner 112 is needed only if detector array 137 is one-dimensional. If detector array 137 is two-dimensional, scanner 112 is not needed.

Figure 5:
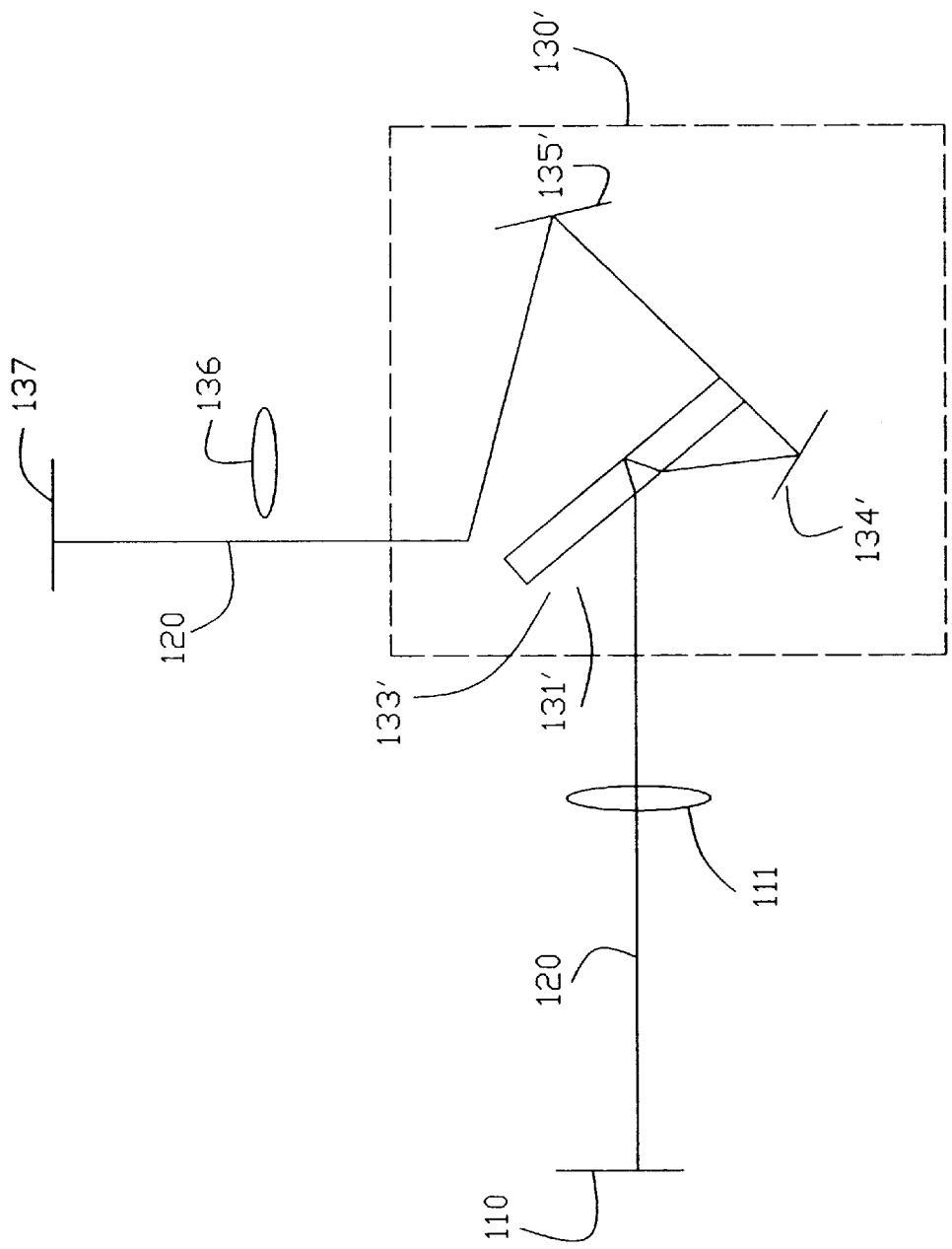
FIG. 5 is a schematic illustration of a prior art imaging spectrometer.

The superiority of the present invention in the context of imaging spectrometers is illustrated in FIG. 5, which shows an imaging spectrometer similar to the imaging spectrometer of FIG. 4 but including a Sagnac interferometer 130' which, like Sagnac interferometer 130, includes two planar reflectors 134' and 135' and a beamsplitter 133', but which rotates rigidly about an axis 131' that runs through beamsplitter 133'. As illustrated, interferometer 130' has been rotated clockwise to the extent that at least one light ray 120, that emerges from optical image source 110 and passes through interferometer 130' as shown, misses focusing lens 136.

Figure 6:
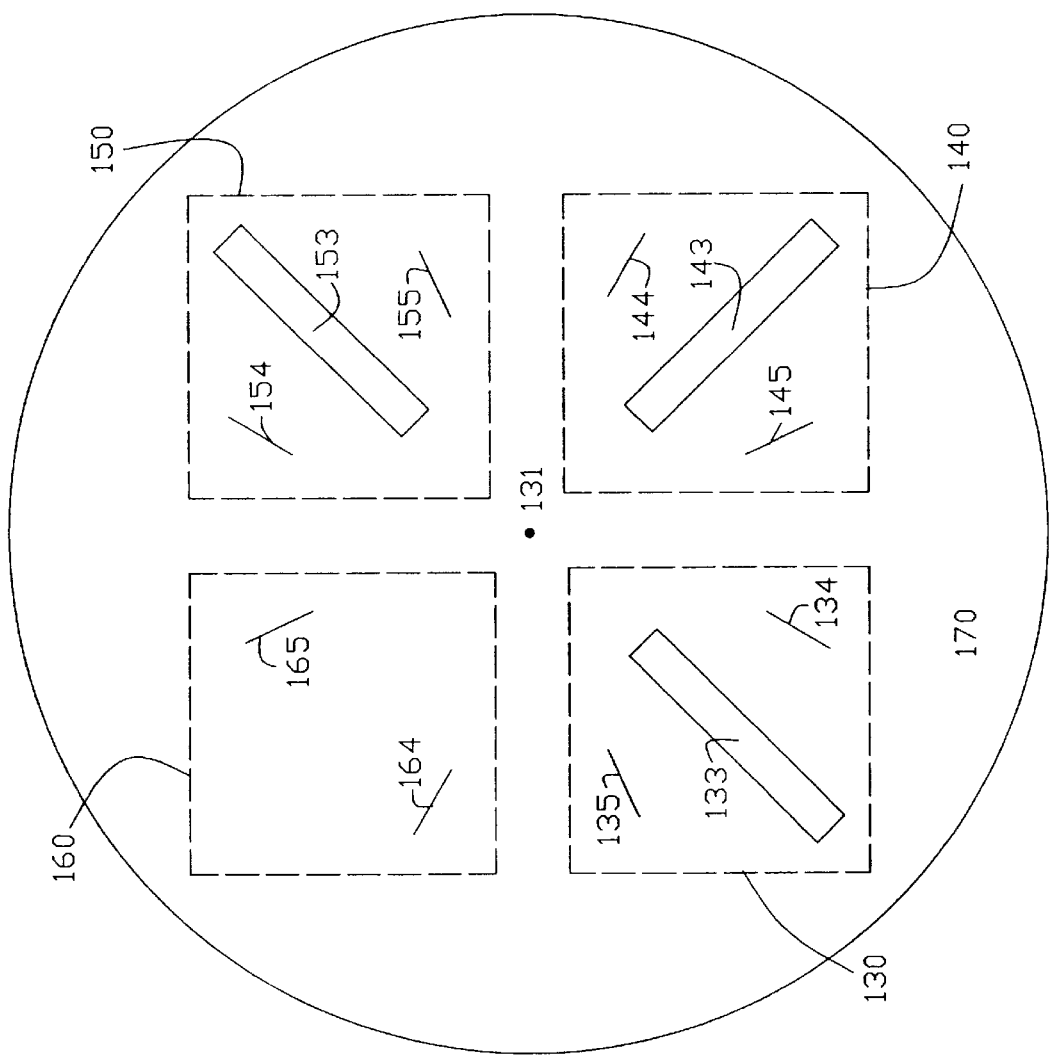
FIG. 6 is a plan view of a most preferred set of interferometers for spectral imaging.

As discussed above in the context of FIG. 2, an imaging spectrometer of the present invention includes several Sagnac interferometers, all with a common axis of rotation. FIG. 6 is a plan view of the most preferred device of the present invention for use with an imaging spectrometer. This device includes three Sagnac interferometers: interferometer 130 of FIG. 4, a second interferometer 140, and a third interferometer 150. In addition, a reflector system 160, that essentially is a Sagnac interferometer without a beamsplitter, is provided. Interferometer 130 includes beamsplitter 133 and reflectors 134 and 135. Interferometer 140 includes a beamsplitter 143 and two planar reflectors 144 and 145. Interferometer 150 includes a beamsplitter 153 and two planar reflectors 154 and 155. Reflector system 160 includes two planar reflectors 164 and 165. All of these components are rigidly mounted on the flat surface of a carousel 170. The reflecting surfaces of reflectors 134, 135, 144, 145, 154, 155, 164 and 165, and the planes of the semireflective layers of beamsplitters 133, 143 and 153, all meet at rotational axis 131 that is perpendicular to the surface of carousel 170. The optical passband of beamsplitter 133 is from 400 nanometers to 800 nanometers, for imaging in the visible part of the spectrum. The optical passband of beamsplitter 143 is from 250 nanometers to 450 nanometers, for imaging in the near ultraviolet. The optical passband of beamsplitter 153 is from 750 nanometers to 1100 nanometers, for imaging in the near infrared. Reflector system 160 is for acquiring a non-spectral reference image of optical image source 110 that is free of interference fringes. Carousel 170 is rotated about axis 131 to position the desired interferometer, or alternatively reflector system 160, in the position with respect to the other components of the imaging spectrometer that is illustrated in FIG. 4 with respect to interferometer 130. Once interferometer 130, 140 or 150 is in place, carousel 170 is rotated about axis 131 to scan the optical path difference.

In a variant of the device of FIG. 6, the passbands of beamsplitters 133, 143 and 153 are entirely in the infrared, including the far infrared. In an imaging spectrometer based on such a device, optical collection system 111 and focusing lens 136 must be replaced by suitable reflective optics, and the detectors of array 137 must be sensitive to the wavelengths being imaged. Typical passbands for such a device are 0.7 to 3.0 microns, 1.0 to 5.5 microns and 5.0 to 14.5 microns.

Figure 7A:
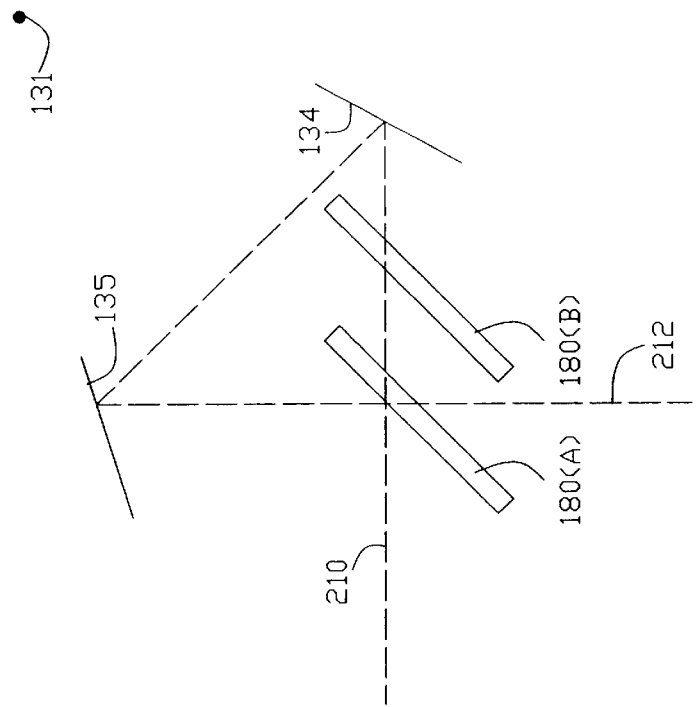
FIG. 7A illustrates a device of the present invention in which the optical elements are two mirrors and a set of filters.
Figure 7B:
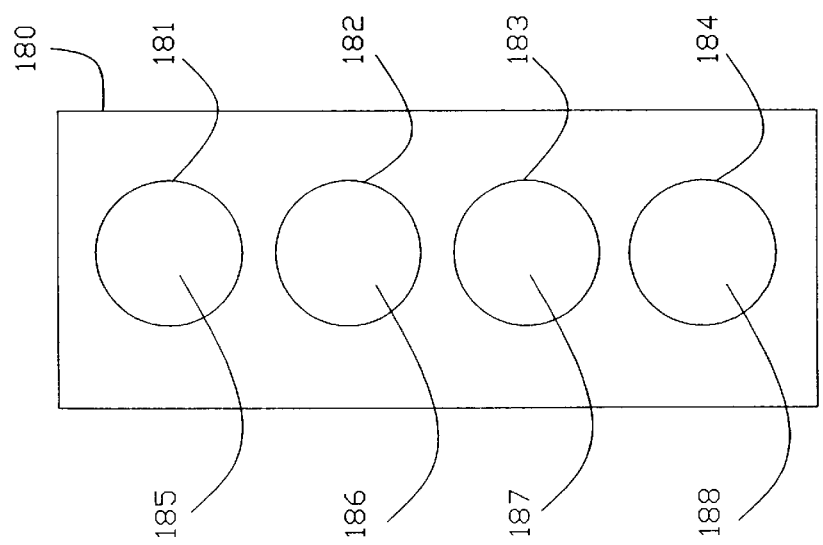
FIG. 7B shows the filter holder of FIG. 7A in more detail.

FIGS. 7A and 7B illustrate a device of the present invention that can be substituted for interferometer 130 to provide images of light source 110 in specific spectral ranges. Instead of beamsplitter 133, the device of FIGS. 7A and 7B includes a rectangular holder 180 of optical filters 185, 186, 187 and 188. Holder 180 has substantially the same exterior dimensions as beamsplitter 133. Holder 180 is opaque except where provided with circular ports 181, 182, 183 and 184 that allow light to traverse respective filters 185, 186, 187 and 188. Each filter 185, 186, 187 or 188 has a different spectral response. The device of FIGS. 7A and 7B is used in applications, such as microscopy, in which incident beam 210 is sufficiently narrow to traverse ports 181, 182, 183 and 184 without being blocked. The device is rotated about point 131 to position any one of filters 185, 186, 187 and 188 in the optical path of incident beam 210, to acquire images of source 110 in the various passbands. Holder 180 is shown in two positions. If holder 180 is in position A, on the bisector of the 45 degree angle formed by reflectors 134 and 135, both incident beam 210 and exit beam 212 traverse the same filter. If holder 180 is in position B, displaced from the bisector, only incident beam 210 traverses the filter. As is well known, the same effect can be achieved using a filter wheel and no mirrors; but the illustrated device is more compact than a filter wheel. It will be appreciated that polarizers may be substituted for one or two of filters 185, 186, 187 and 188 for acquiring images of differently polarized components of the light from source 110.

Figure 8:
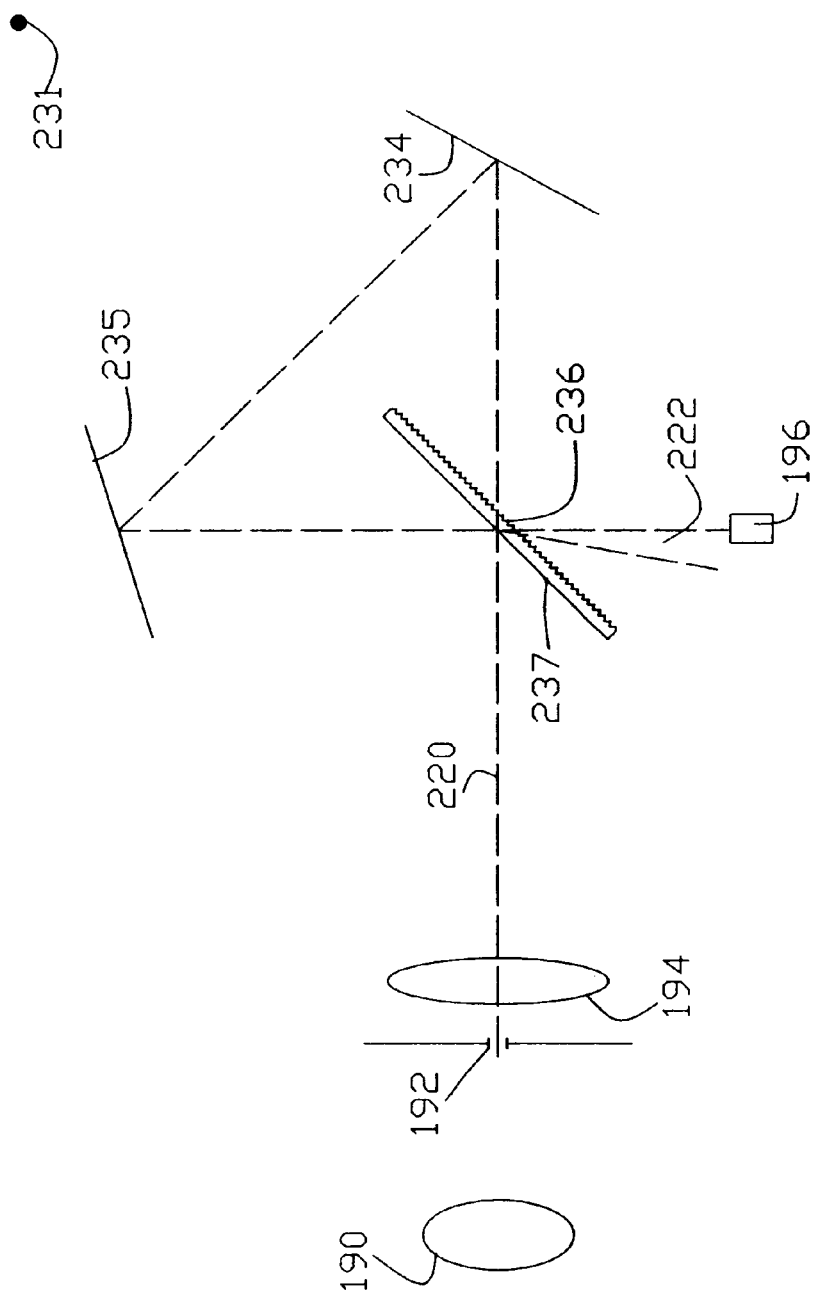
FIG. 8 illustrates a non-imaging spectrometer of the present invention.

FIG. 8 illustrates a non-imaging spectrometer of the present invention. This device is based on two planar reflectors 234 and 235 and a planar, single-sided diffraction grating 236. As in all devices of the present invention, planes defined by reflectors 234 and 235 and diffraction grating 236 meet at a rotation axis 231, with the planes defined by reflectors 234 and 235 meeting at a 45° angle and the plane defined by diffraction grating 236 bisecting that angle. Light from a source 190 passes through a slit 192 and is collimated by an optical system represented symbolically by a lens 194, to form an incident beam 220. The back side 237 of diffraction grating 236 is smooth and reflective, so incident beam 220 is reflected, first to reflector 235, thence to reflector 234, and thence back to the front side of diffraction grating 236. Some of the light incident on the front side of diffraction grating 236 is reflected specularly, at a right angle to incident beam 220, but some of the light incident on the front side of diffraction grating 236 is diffracted, at a small, wavelength-dependent angle to the specularly reflected light, to form a first order diffracted fan 222. Rotating reflectors 234 and 235 and diffraction grating 236 rigidly about rotation axis 231 causes fan 222 to sweep across a detector 196. At each rotational position of reflectors 234 and 235 and diffraction grating 236, detector 196 receives light of a different wavelength, so in the course of the rotation, the spectrum of incident beam 220 is scanned. In a variant of this device, diffraction grating 236 is two sided, to provide even wider angular separation of the various wavelengths in fan 222.

While the invention has been described with respect to a limited number of embodiments, it will be appreciated that many variations, modifications and other applications of the invention may be made.

What is claimed is:

1. A method for simultaneously measuring the spectral intensity as a function of wavelength of all the pixels of a two-dimensional scene while detecting a real and stationary image of the scene, the method comprising the steps of:

(a) collecting incident light simultaneously from all points of the two-dimensional scene using collimating optics;

(b) passing said incident collimated light through an inferometer system including:

(i) a first element defining a first plane, said first element including a reflector;

(ii) a second element defining a second plane and fixed rigidly with respect to said first element, said second element including a reflector, said first and second planes intersecting, along an axis, at an angle of between about 42 degrees and about 48 degrees, and (iii) a third element defining a third plane and fixed rigidly with respect to said first and second elements so that said axis is included in said third plane, said third element including a beamsplitter, so that said light is first split into two coherent beams which travel along different optical paths inside said inferometer and then said two coherent beams recombine to interfere with each other to form an exiting light;

(c) passing said exiting light through a focusing optical system which focuses said exiting light on a detector having an array of detector elements, so that at each instant each of said detector elements is the image of one and always the same pixel of said scene for the entire duration of the measurement, so that the real image of the scene is stationary on the detector array at any time during the measurement the image is still visible and recognizable, and so that each of said detector elements produces a signal which is a particular linear combination of light intensity emitted by said pixel at different wavelengths, wherein said linear combination is a function of instantaneous optical path difference;

(d) rotating said elements of said inferometer system rigidly about said axis, so that said optical path difference between said two coherent beams generated by said inferometer system is scanned simultaneously for all the pixels of the scene; and (e) recording said signals of each of said detector elements as functions of time using a recording device.

2. The method of claim 1, wherein said angle is about 45 degrees.

3. The method of claim 1, wherein said third plane bisects said angle.

4. The method of claim 1, wherein said array of detector elements is two dimensional.

5. The method of claim 1, wherein said array of detector elements is one dimensional, the method further comprising the step of:
(f) scanning said collimated light, so that only a substantially one-dimensional portion of said collimated light is passed through said interferometer system at one time.

6. The method of claim 1, wherein said incident light, prior to entering said interferometer system, is passed through an afocal telescope which simultaneously collects and collimates said light for each of the pixels of the scene.

7. The method of claim 1, wherein said incident light, prior to entering said interferometer system, is passed through a microscope which simultaneously collects and collimates said light for each of the pixels of the scene.

8. The method of claim 1, wherein said incident light, prior to entering said interferometer system, is passed through a fundus camera which simultaneously collects and collimates said light for each of the pixels of the scene.

9. The method of claim 1, wherein said incident light, prior to entering said interferometer system, is passed through an endoscope which simultaneously collects and collimates said light for each of the pixels of the scene.

10. A method for simultaneously measuring the spectral intensity as a function of wavelength of all the pixels of a two-dimensional scene located at infinity while detecting a real and stationary image of the scene, the method comprising the steps of:
(a) collecting naturally collimated incident light simultaneously from all points of the two-dimensional scene;
(b) passing said incident naturally collimated light through an inferometer system including:
(i) a first element defining a first plane, said first element including a reflector;
(ii) a second element defining a second plane and fixed rigidly with respect to said first element, said second element including a reflector, said first and second planes intersecting, along an axis, at an angle of between about 42 degrees and about 48 degrees, and
(iii) a third element defining a third plane and fixed rigidly with respect to said first and second elements so that said axis is included in said third plane, said third element including a beamsplitter,
so that said light is first split into two coherent beams which travel along different optical paths inside said inferometer and then said two coherent beams recombine to interfere with each other to form an exiting light;
(c) passing said exiting light through a focusing optical system which focuses said exiting light on a detector having an array of detector elements, so that at each instant each of said detector elements is the image of one and always the same pixel of said scene for the entire duration of the measurement, so that the real image of the scene is stationary on the detector array at any time during the measurement the image is still visible and recognizable, and so that each of said detector elements produces a signal which is a particular linear combination of light intensity emitted by said pixel at different wavelengths, wherein said linear combination is a function of instantaneous optical path difference;
(d) rotating said elements of said inferometer system rigidly about said axis, so that said optical path difference between said two coherent beams generated by said inferometer system is scanned simultaneously for all the pixels of the scene; and
(e) recording said signals of each of said detector elements as functions of time using a recording device.

11. The method of claim 10, wherein said array of detector elements is two dimensional.

12. The method of claim 10, wherein said array of detector elements is one dimensional, the method further comprising the step of:
(f) scanning said collimated light, so that only a substantially one-dimensional portion of said collimated light is passed through said interferometer system at one time.

13. An apparatus for simultaneously measuring the spectral intensity as a function of wavelength of all the pixels of a two-dimensional scene while detecting a real and stationary image of the scene, comprising:
(a) an inferometer system for receiving collected incident collimated light simultaneously from all points of the two-dimensional scene, said light being first split into two coherent beams which travel in different directions inside said inferometer and then said two coherent beams recombine to interfere with each other to form an exiting light, said inferometer system including:
(i) a first element defining a first plane, said first element including a reflector;
(ii) a second element defining a second plane and fixed rigidly with respect to said first element, said second element including a reflector, said first and second planes intersecting, along an axis, at an angle of between about 42 degrees and about 48 degrees, and
(iii) a third element defining a third plane and fixed rigidly with respect to said first and second elements so that said axis is included in said third plane, said third element including a beamsplitter,
said elements being rotatable about said axis so that an optical path difference between said two coherent beams generated by said inferometer system is scanned simultaneously for all the pixels of the scene;
(b) a focusing optical system through which said exiting light is passed to form a focused light;
(c) a detector having an array of detector elements on which said focused light is directed, so that at each instant each of said detector elements is the image of one and always the same pixel of said scene for the entire duration of the measurement, so that the real image of the scene is stationary on the detector array and so that each of said detector elements produces a signal which is a particular linear combination of light intensity emitted by said pixel at different wavelengths, wherein said linear combination is a function of the instantaneous optical path difference; and
(d) a recording mechanism for receiving said signals of each of said detector elements as a function of time using a recording device.

14. The apparatus of claim 13, wherein said array of detector elements is two dimensional.

15. The apparatus of claim 13, wherein said array of detector elements is one dimensional, and wherein the apparatus further comprises:
(e) a mechanism for scanning said collimated light, so that only a substantially one-dimensional portion of said collimated light is passed through said interferometer system at one time.

16. The apparatus of claim 13, further comprising:
(e) a mechanism, for collecting and collimating light from the two dimensional scene, wherefrom said interferometer system receives said collected incident collimated light.

17. The apparatus of claim 16, wherein said collecting and collimating mechanism is selected from the group consisting of telescopes, microscopes, fundus cameras and endoscopes.

* * * * *